United States Patent [19]

Schreiber et al.

[11] 4,314,070

[45] Feb. 2, 1982

[54] PROCESS FOR PRODUCING META-PHENOXYBENZOIC ACIDS AND ESTERS

[75] Inventors: Fred G. Schreiber, Highland Park; Peter S. Gradeff, Pottersville, both of N.J.

[73] Assignee: Rhone-Poulenc Inc., Monmouth Junction, N.J.

[21] Appl. No.: 149,588

[22] Filed: May 14, 1980

[51] Int. Cl.$^3$ ............................................. C07C 69/92
[52] U.S. Cl. ..................................... 560/64; 560/21; 560/65; 560/109; 562/473; 568/630; 568/648; 568/649
[58] Field of Search ............................ 560/64, 21, 65; 568/635

[56] References Cited

U.S. PATENT DOCUMENTS 3,487,114  12/1969  Irick et al. ........................... 568/635
3,769,320  10/1973  Chodnekar et al. ................... 560/64

FOREIGN PATENT DOCUMENTS 9451  of 1914  United Kingdom ................ 568/635
2025403  1/1980  United Kingdom ................ 568/635

OTHER PUBLICATIONS

A. A. Moroz et al. Russian Chem. Reviews, 43 (8) 1974.
Ullman and Sponager *Ber. Deut. Chem.* Ges. 38 2211 (1905).
Tomita, M. et al., *J. Pharm. Soc. Japan,* 74 1061–1065, 1278 (1954).

*Primary Examiner*—Paul J. Killos

[57] ABSTRACT

An improved process for producing meta-phenoxy benzoic acids and their lower alkyl esters in improved yields and with higher selectivity by reacting an alkali metal phenate with a lower alkyl ester of meta-halobenzoic acid in the presence of a copper sulfate catalyst.

13 Claims, No Drawings

PROCESS FOR PRODUCING META-PHENOXYBENZOIC ACIDS AND ESTERS

BACKGROUND OF THE INVENTION

Meta-phenoxybenzoic acid and its lower alkyl esters are the simplest representatives of a group of compounds that differ by the substituents on either of the two benzene moieties. Some of these chemicals have been noted for their herbicide properties, others are used as intermediates in preparing commercially important herbicides.

The reaction between the alkali metal salt of phenol or a substituted phenol and the m-halobenzoic lower alkyl ester or substituted ones has been used in most of the syntheses. This general reaction is known as the Ullmann ether synthesis as it was reported first by Ullman and Sponagel, Ber. Deut. Chem. Ges., 38 2211 (1905).

Only two references were found, however, that refer to the particular preparation of the methyl m-phenoxybenzoate by the Ullmann Syntheses: J. Pharm. Soc. Japan, 74, 1061 (1954) and J. Pharm. Soc. Japan, 74, 1728 (1954). In both of them, the m-bromo analog is used in the presence of a catalyst consisting of copper and cupric acetate. In both cases, the reported yields were rather low, namely 39 and 22 percent, respectively.

It is, accordingly, the main objective of the present invention to provide a process for the preparation of m-phenoxybenzoic acid or its lower alkyl esters or substituted derivatives thereby by the Ullmann reaction, but in the presence of a catalyst that will provide the reaction under milder conditions and higher yields.

Other objectives of the invention will be apparent to those skilled in the art from the present description.

In the course of the research which resulted in the process of the present invention, the reaction of methyl m-chlorobenzoate and sodium phenate was used at first in the screening of the possible catalyst candidates. It was surprising that better results were obtained in carrying the reaction without any catalyst, than when using the copper salt catalysts disclosed in the above-mentioned references.

It was soon recognized that the greatest obstacle to good yields was the concurrent saponification of the starting material, yielding anisole instead of the desired ether. A transesterification of the methyl ester with the phenate is another side reaction. A variety of copper, as well as non-copper catalysts, was tried. It was discovered that copper sulfate was the only catalyst which provided distinctly superior yields.

GENERAL DESCRIPTION OF THE INVENTION

The process of the present invention can be represented by the following reaction scheme in which the principal and desired product is a meta-phenoxybenzoic acid or its lower alkyl ester.

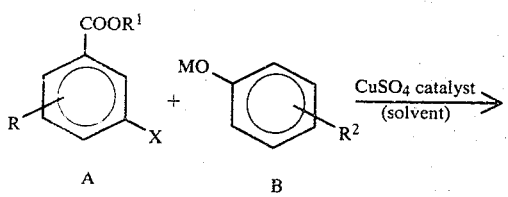

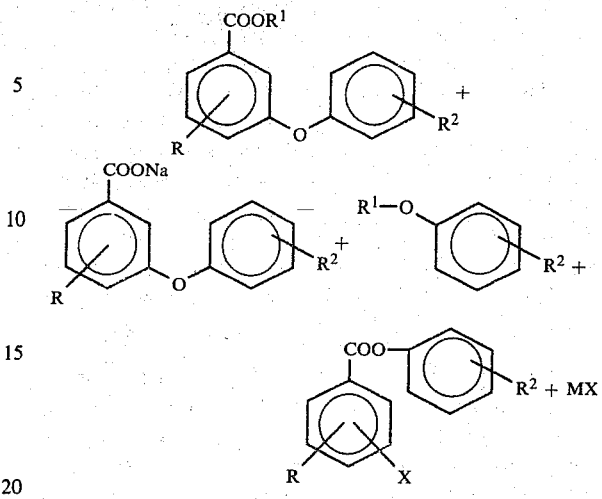

wherein
X is a halogen, such as Cl, Br, I, F;
R is H, alkyl, cycloalkyl, aryl, $NO_2$;
$R^1$ is a lower alkyl group, such as methyl, ethyl, propyl, isopropyl, butyl, isobutyl, amyl;
$R^2$ is H, p-Me, p-MeO, p-Cl, p-t-butyl, o-MeO, 2,4-dimethyl, p-F, p-$CF_3$; and
M is Na or K.

In the process, an alkali metal, such as sodium or potassium, can be used to prepare the phenate. It will be more economical to use alkali hydroxides instead, and azeotropically remove the water that is formed. This can be done in an excess of phenol or in the presence of a high boiling solvent such as xylene. Any solvent that would be inert otherwise can be used, provided that it permits the maintenance of the desired reaction temperature. A lower boiling inert solvent can also be used if the reaction is carried in a closed system and consequently under pressure. The amount of alkali metal or hydroxide is preferably approximately equivalent to the amount of m-halobenzoate. It is obvious that smaller amounts can be used, but any advantage in selectivity is lost by reduced productivity of the desired compound. The solvent provides a vehicle for the stirring of the phenate, which is a solid. After the addition of the halo ester, some of the solvent may be distilled to permit increasing the temperature of the reaction mixture.

Commercial grade cupric sulfate hydrate provides improved results, but it is preferably to use anhydrous grade, which simply can be made by drying the hydrate at sufficiently high temperature to eliminate all water. The amount of copper sulfate catalyst employed is desirably between about 0.01 and about 0.6 mole of copper sulfate catalyst per mole of meta-halobenzoic acid or ester starting material, preferably between about 0.1 and 0.3 mole.

The catalyst and m-halo ester to be reacted are desirably added to the phenate at a temperature of about 140° C. The temperature is raised to about 160°–180° C. and maintained at this temperature for about several hours.

The reaction temperature is desirably from about 100° to 240° C., and preferably between about 140° and 200° C. At lower temperatures, the reaction is rather slow. At higher temperatures, the reaction loses some selectivity, but is faster. From about 4 to 24 hours reaction time is generally sufficient with possibly longer times, particularly at lower temperatures. Most reactions are completed in about 6 to 16 hours.

The work-up of the reaction mixture for recovery of the desired product depends on the final product desired. Treatment with aqueous base or acid will hydrolyze all ester product and starting material to the corresponding acid which is then isolated. Or, if the ester is the desired product, all acids that might be present in the reaction mixture as a result of saponification during the reaction are esterified by methylation and then isolated. This will be shown in the examples which follow.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Sodium phenate (1.08 moles) was generated from sodium metal and phenol in 300 ml. xylene at reflux. One hundred mls. of xylene were distilled off and then cupric sulfate (17.8 g.) and methyl m-chlorobenzoate (170.6 g.) were added. More xylene was distilled out until the internal temperature was 165° C. and then the reaction mixture was refluxed overnight. The reaction mixture was cooled, methylated with dimethyl sulfate, and again refluxed overnight.

The reaction mixture was cooled, diluted with water, and filtered. The organic layer was washed with water, dried, filtered, and concentrated. The crude product was flash distilled to give a direct yield of 67.5 percent and a true yield of 86.2 percent by weight of m-phenoxybenzoic acid methyl ester.

EXAMPLE 2

Sodium phenate (0.156 mole) was generated from 16 g. phenol and 3.6 g. sodium in xylene under argon. Copper sulfate (2.5 g.) and 30 g. of isopropyl ester of m-chloro-benzoic acid were added. Some xylene was distilled off until the internal temperature reached 150° C. Internal temperature was maintained at 170° C. for 21 hours. The mixture was cooled, methylated with 5 mls. of dimethyl sulfate in 100 mls. acetone and refluxed overnight.

The reaction mixture was cooled, filtered, and the filtrate concentrated by evaporation. The solids from the filtration were dissolved in water, acidified, and the aqueous layer extracted with methylene chloride. This extract was combined with the concentrate and the whole washed with water. After drying, the solution was concentrated. The crude oil was flashed at 0.05 mm. of mercury vacuum. Direct yield of m-phenoxybenzoic acid isopropyl ester was 69.2 percent. The true yield was 83.4 percent.

EXAMPLE 3

Example 1 was repeated, with sodium being replaced by potassium. The results obtained were comparable.

EXAMPLES 4 TO 11

Similarly to Example 1, when phenates having differing $R^2$ substituents were employed, the corresponding expected m-phenoxy derivatives were obtained.

| Example No. | $R^2$-substituent |
| --- | --- |
| 4 | p-Me |
| 5 | p-MeO |
| 6 | p-Cl |
| 7 | p-t-butyl |
| 8 | o-MeO |
| 9 | 2,4-dimethyl |
| 10 | p-F |
| 11 | p-CF |

EXAMPLE 12

Similarly to Example 1, when methyl m-bromo benzoic ester replaced the corresponding m-chloro starting material, the expected phenoxy derivative was obtained.

EXAMPLE 13

In a series of experiments reacting 5 g. of methyl meta-chlorobenzoate and 4.3 g. of sodium phenate using varying amounts of copper sulfate catalyst, it was found that the beneficial action of the catalyst can be detected in amounts of as little as about 0.01 mole of copper sulfate per mole of meta-halobenzoate ester starting material. It was found that the preferable range is between 0.1 and 0.3 mole of catalyst per mole of ester starting material, and the yields decrease as one employs in excess of 0.3 mole of catalyst per mole of benzoate ester starting material. Amounts of copper sulfate catalyst in excess of 0.6 mole per mole of meta-halobenzoate ester were found not to be beneficial.

The terms and expressions which have been employed are usd as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process for producing meta-phenoxybenzoic acids and their lower alkyl esters, which comprises reacting an alkali-metal phenate with a lower alkyl ester of meta-halobenzoic acid in the presence of a copper sulfate catalyst.

2. A process according to claim 1, wherein sodium phenate is reacted with meta-chlorobenzoic acid methyl ester.

3. A process according to claim 1, wherein the alkali metal phenate is a member selected from sodium phenate and potassium phenate.

4. A process according to claim 1, wherein the alkali metal phenate is substituted with a substituent selected from the class consisting of p-methyl, p-methoxyl, p-chloro, p-t-butyl, ortho-methoxyl, 2,4-dimethyl, p-F, and p-CF$_3$.

5. A process according to claim 1, wherein the temperature is between about 110° and 240° C.

6. A process according to claim 1, wherein the temperature is between about 140° and 200° C.

7. A process according to claim 1, wherein sodium phenate is reacted with a lower alkyl ester of meta-chlorobenzoic acid.

8. A process according to claim 1, wherein the lower alkyl ester of meta-halobenzoic acid is substituted with a substituent selected from the class consisting of alkyl, cycloalkyl, aryl and nitro.

9. A process according to claim 1, wherein the copper sulfate and the lower alkyl ester of meta-halobenzoic acid are added to a solution of the alkali metal phenate dissolved in an inert organic solvent.

10. A process according to claim 1, wherein the amount of copper sulfate catalyst is between about 0.01 and 0.6 moles per mole of lower alkyl ester of m-halobenzoic acid starting material.

11. A process according to claim 1, wherein the amount of copper sulfate catalyst is between about 0.1 and 0.3 mole per mole of lower alkyl ester of meta-halobenzoic acid starting material.

12. A process according to claim 1, wherein the copper sulfate used is cupric sulfate.

13. A process according to claim 12, wherein the cupric sulfate is anhydrous.

* * * * *

UNITED STATES PATENT AND TRADEMARK OFFICE
CERTIFICATE OF CORRECTION

PATENT NO. : 4,314,070
DATED : February 2, 1982
INVENTOR(S) : Schreiber et al.

It is certified that error appears in the above—identified patent and that said Letters Patent is hereby corrected as shown below:

Col. 2, line 50 - "preferably" should be --preferable--.

Col. 4, line 39 - "usd" should be --used--.

Signed and Sealed this

Seventeenth Day of August 1982

[SEAL]

Attest:

GERALD J. MOSSINGHOFF

*Attesting Officer*     *Commissioner of Patents and Trademarks*